(12) United States Patent
Lacza et al.

(10) Patent No.: US 9,381,272 B2
(45) Date of Patent: Jul. 5, 2016

(54) METHOD FOR PRODUCING AN IMPLANTABLE BONE COMPOSITION

(71) Applicants: Zsombor Lacza, Csopak (HU); Miklós Weszl, Budapest (HU)

(72) Inventors: Zsombor Lacza, Csopak (HU); Miklós Weszl, Budapest (HU)

(73) Assignee: Lacerta Technologies Inc., Raleigh, NC (US)

( * ) Notice: Subject to any disclaimer, the term of this patent is extended or adjusted under 35 U.S.C. 154(b) by 0 days.

(21) Appl. No.: 14/047,758

(22) Filed: Oct. 7, 2013

(65) Prior Publication Data

US 2014/0044792 A1    Feb. 13, 2014

Related U.S. Application Data

(63) Continuation-in-part of application No. 12/811,031, filed as application No. PCT/IB2009/050783 on Feb. 26, 2009, now Pat. No. 8,551,170.

(30) Foreign Application Priority Data

Feb. 26, 2008    (HU) ...................... 0800134

(51) Int. Cl.
| | |
|---|---|
| A61F 2/28 | (2006.01) |
| A61L 2/00 | (2006.01) |
| A61K 33/00 | (2006.01) |
| A61F 13/00 | (2006.01) |
| A61L 27/38 | (2006.01) |
| A61L 27/36 | (2006.01) |
| A61L 27/34 | (2006.01) |

(52) U.S. Cl.
CPC ............. *A61L 27/3834* (2013.01); *A61L 27/34* (2013.01); *A61L 27/365* (2013.01); *A61L 27/3608* (2013.01); *A61L 27/3691* (2013.01); *A61L 27/3695* (2013.01); *A61L 27/3847* (2013.01); *A61L 2430/02* (2013.01)

(58) Field of Classification Search
USPC ......... 424/422, 423; 530/830, 840; 623/16.11
See application file for complete search history.

(56) References Cited

U.S. PATENT DOCUMENTS

| | | |
|---|---|---|
| 4,902,296 A | 2/1990 | Bolander et al. |
| 6,224,913 B1 | 5/2001 | Ducheyne et al. |
| 2001/0018614 A1 | 8/2001 | Bianchi |

OTHER PUBLICATIONS

Weszl et al., Freeze-Dried Human Serum Albumin Improves the Adherence and Proliferation of Mesenchymal Stem Cells on Mineralized Human Bone Allografts Journal of Orthopaedic Research vol. 30, Issue 3, pp. 489-496, Mar. 2012.*
Horvathy et al.,Serum albumin coating of demineralized bone matrix results in stronger new bone formation J Biomed Mater Res B Appl Biomater. Feb. 10, 2015. pp. 1-7.*
Costain et al Fresh-frozen vs. irradiated allograft bone in orthopaedic reconstructive surgery Injury vol. 40, Issue 12, Dec. 2009, pp. 1260-1264.*
Hofmann et al The influence of bone allograft processing on osteoblast attachment and function Journal of Orthopaedic Research 23 (2005) 846-854.*
Peters (Advances in Clinical Chemistry vol. 13, 1970, Abstract.*
Cancedda et al.: "Tissue engineering and cell therapy of cartilage and bone", Matrix Biology, 2003, vol. 22, pp. 81-91.
Bierbaum et al.: "Modification of Ti6Al4V surfaces using collagen, I, III, and fibronectin. II. Influence on osteoblast responses", Journal of Biomedical Materials Research, 2003, vol. 67A, pp. 431-438.

* cited by examiner

*Primary Examiner* — Maria Leavitt
(74) *Attorney, Agent, or Firm* — Jason D. Voight

(57) ABSTRACT

Methods for producing implantable bone compositions suitable for attaching stem cells thereto, characterized in that bone particles are contacted with an albumin comprising solution. Said bone particles can be mineralized and/or lyophilized bone particles of animal or human origin. Preferably the non-immunogenic albumin comprising solution is lyophilized onto said bone particles. The invention further concerns bone compositions suitable for using in graft implantation obtainable by said methods.

17 Claims, 11 Drawing Sheets

METHOD FOR PRODUCING AN IMPLANTABLE BONE COMPOSITION

This is a continuation-in-part of application Ser. No. 12/811,031, which is the National Phase of PCT/IB2009/050783, filed Feb. 26, 2009, now U.S. Pat. No. 8,551,170, issued Oct. 8, 2013, the entire disclosure of which is hereby incorporated by reference herein.

FIELD OF THE INVENTION

The invention relates to methods for producing implantable bone compositions suitable for attaching stem cells thereto, characterized in that bone particles are contacted with an albumin comprising solution. Said bone particles can be mineralized and/or lyophilized bone to particles of animal or human origin. In a preferred embodiment the non-immunogenic albumin comprising solution is lyophilized onto said bone particles. The invention further concerns bone compositions suitable for use in graft implantation obtainable by said methods.

BACKGROUND OF THE INVENTION

Bone grafts are one of the most common transplanted tissues. Worldwide more than 2.2 million bone-grafting procedures are performed annually to repair bone defects in orthopedics, neurosurgery and dentistry (9, 10, 12, 13). Bone autografts and allografts are conventionally used to replace the bone defects.

Autografts are the gold standard to fill the bone defects, because they provide the fastest incorporation without immunological complications (15, 17). Few mature osteoblasts survive the transplantation however the number of precursor cells that stay alive is adequate. The osteogenic potential is derived from these precursor cells. It is well known in the art that there are severe limitations for the use of autografts these include the increased operative time, limited availability and significant morbidity related to blood loss, wound complications, local sensory loss and, most importantly, chronic pain (14, 16, 18, 19).

Allografts as an alternative approach offer similar characteristics with the exclusion of osteogenic cells (9, 10). There is not a standard rule related to the preparation of bone allografts thus several types of them are disclosed in publications, like fresh, fresh-frozen, freeze-dried or demineralized bone allografts (9, 10). Allografts possess osteoconductive and osteoinductive properties but the latter may not be recognized unless the graft is utilized in either morsellized or demineralized form. Complications associated with allografts include fracture, non-union, immunological complications and infection.

Urist and others (3, 20, 21, 22, 23, 24) demonstrated the effect of demineralized bone matrix or bone morphogenetic protein in bone induction. They also demonstrated that the active components of the demineralized bone matrix are the low molecular weight proteins (LMWPs). Bolander et al. (1, 2) coated the demineralized bone graft with additional low molecular weight proteins. This method could enhance osteoinductive potential of the graft. Nowadays, the demineralized allograft is still regarded as the most appropriate allogenic substitute for replace bone defects because it possesses osteoinductive and osteoconductive ability, however, its mechanical properties are not adequate (22). In addition manufacturing of demineralized bone matrix with constant high osteoinductive property is still a challenge. The mineralized or non demineralized bone allografts, for instance freeze-dried, fresh or fresh-frozen allografts possess good mechanical property but their osteoinductive capability is much poor compared with demineralized bone matrix. Rust et al. (4) demonstrated that mesenchymal stem cells (MSC) could differentiate into osteoblasts on the surface of a mineralized bone allograft, which contains the original proteins of normal bone. They found that MSCs could not differentiate on the surface of heat-treated allografts. This observation shows that particular bone proteins may play a key role in the adherence and commitment of MSCs. Booland et al. (5) proved that cells survive the impaction force on the mineralized allograft, which might be during the clinical use. Lewandrowski et al. (6) coated cortical bone grafts with biopolymers to support the adherence of periosteal derived bone cells on the graft's surface.

New biomaterials combined with osteogenic cells are now being developed as an alternative to bone grafts (11). The biomaterials are created to build up a three-dimensional scaffold to which cells can adhere, proliferate and differentiate into functional osteogenic cells (7, 9). Ore et al. (8) demonstrated that the enhanced differentiation of the human bone marrow derived cells on a 70% carbonated apatite, which has a composition similar to bone minerals.

Present inventors previously found that coating of spongy bone with proteins that are known to help cell adherence had not always helped cell adherence onto the bone. While coating with fibronectin increased the number of attached cells, coating with collagen did not help in increasing the number of attached cells. Moreover none of them supported the proliferation of the attached cells.

An optimal graft should have all the advantages of allo-, and autografts, including osteoinductive ability, good mechanical property and immunological compatibility with the host (10, 11). Furthermore preferably it is easily available and does not cause operative burden to harvest it, like autografts.

Our aim was to develop a reliable and safe coating method that ensures the attachment of stem cells onto the surface of mineralized bone allografts. In other words, the object of the present invention was to develop new methods that provide bone grafts that are compatible with the host and do not cause any immunologic complications while at the same time are easily available.

SUMMARY OF THE INVENTION

Present inventors solved the above problem according to a preferred embodiment of the invention by coating bone allografts of human or animal origin with albumin, advantageouslyhuman serum albumin dried, advantageously freeze-dried onto their surface. This preferred embodiment of the present invention provided excellent conditions for not just the attachment but also for the proliferation of stem cells e.g. mesenchymal stem cells (MSC).

The present invention relates to a method for producing implantable bone composition suitable for attaching stem cells thereto, characterized in that bone particles are contacted with a protein solution comprising albumin. While the concentration of albumin in said solution is not a strict limiting factor, preferably said albumin comprising solution is an albumin solution comprising 1 to 50% albumin, preferably 3 to 30% albumin, more preferably 5 to 25% albumin and most preferably approximately 10% albumin, wherein the percentages are weight/weight percentages. Preferably said albumin is human albumin and more preferably human albumin of serum origin. Further preferably, said albumin is isolated from the serum of the patient intended to receive, as a transplantation, the implantable bone composition of the invention. According to a preferred embodiment of the invention said bone particles are lyophilized bone particles and/or mineralized bone particles that are substantially cleaned from organic components.

In a preferred embodiment said albumin comprising solution is dried onto said mineralized bone composition and in a further preferred embodiment said drying is made by lyophilization. Said bone particles can be of human or animal origin.

Advantageously in the above method some of the ingredients of said albumin comprising solution is/are of human origin or is/are immunologically humanized and/or said albumin comprising solution is obtained from a patient in need of bone implantation. Preferably said albumin comprising solution comprises the serum of said patient or any fraction of said serum.

According to a further preferred embodiment of the present invention said albumin comprising solution preferably comprises recombinant albumin, wherein said albumin comprising solution optionally further comprises fibronectin or collagen or combination thereof.

Advantageously said protein solutions are free from components being potentially immunogenic to patients to whom said bone composition according to the invention is designed for. Methods for analyzing potential immunogenicity of a protein solution are well known in the art.

The invention concerns a method wherein the above methods further comprise a step of attaching cells capable of enhancing bone formation onto the surface of said bone particles.

In a preferred embodiment of the present invention in the above methods said cells capable of enhancing bone formation are obtained from a patient in need of a bone implantation, preferably said cells are mesenchymal stem cells (MSCs).

The invention further relates to a bone composition suitable for use in graft implantation, obtainable by the above methods of the invention.

The implantable bone compositions of the invention advantageously comprise albumin at less than 10 weight percent of the composition and are, advantageously, in the form of loose bone chips or bone blocks and not in the form of a conglomerate malleable mass.

The invention still further relates to the use of said compositions in therapy.

A graft prepared from a bone composition according to the present invention combines the beneficial properties of allo-, and autografts. Human mineralized bone allograft was used as a scaffold. A person skilled in the art would appreciate that instead of human mineralized bone allografts mineralized allografts of animal origin could be used equally well. The human allograft was cleaned from the bone original proteins. In this manner, the scaffold provides good mechanical stability to the graft; furthermore since it is mineralized it decreases the chance of any immunological complication. The scaffold's surface is coated with proteins of human origin, like fibronectin or albumin to supply the seeded adherence of human MSCs and proliferation. Surprisingly we found that coating with a serum solution (Fetal Calf Serum, FCS) helped the adherence of MSC to an even greater extent. The coating is necessary for cell viability on the allograft of the present invention and lyophilization of such proteins or protein solutions onto the bone enhanced the number of cells which were attached and supported their proliferation as well. In a preferred embodiment of the present invention the graft consists of materials of human origin, like autologous albumin and MSCs. This property could enable for the graft of the invention fast incorporation into the host without immunological complications, and could support an early recovery of patients.

BRIEF DESCRIPTION OF THE DRAWINGS

FIG. 2A shows the measured fluorescence 3, 10 and 18 days following the addition of MSCs, caused by the adhered cells on the surface of allografts onto which collagen type I was lyophilized, while

FIG. 3A shows the measured fluorescence 3, 10 and 18 days following the addition of MSCs, caused by the adhered cells on the surface of allografts onto which fibronectin was lyophilized, while

FIG. 4A shows the measured fluorescence 3, 10 and 18 days following the addition of MSCs, caused by the adhered cells on the surface of allografts onto which collagen type I and fibronectin was lyophilized, while

FIG. 6A shows the measured fluorescence 3, 10 and 18 days following the addition of MSCs, caused by the adhered cells on the surface of allografts onto which human albumin was lyophilized, while

FIG. 7A shows the measured fluorescence 3, 10 and 18 days following the addition of MSCs, caused by the adhered cells on the surface of allografts onto which human albumin and fibronectin was lyophilized, while

FIG. 8A shows the measured fluorescence 3, 10 and 18 days following the addition of MSCs, caused by the adhered cells on the surface of allografts onto which fetal calf serum was lyophilized, while

FIG. 10A shows the surface of rat bone allograft coated with lyophilized human albumin which dose not contain adhered stem cells (act as control), while

FIG. 11A-B show micro-CT snapshots of the inserted PMMA spacer between the dissected bone ends, while

DETAILED DESCRIPTION OF THE INVENTION

Figure 1:
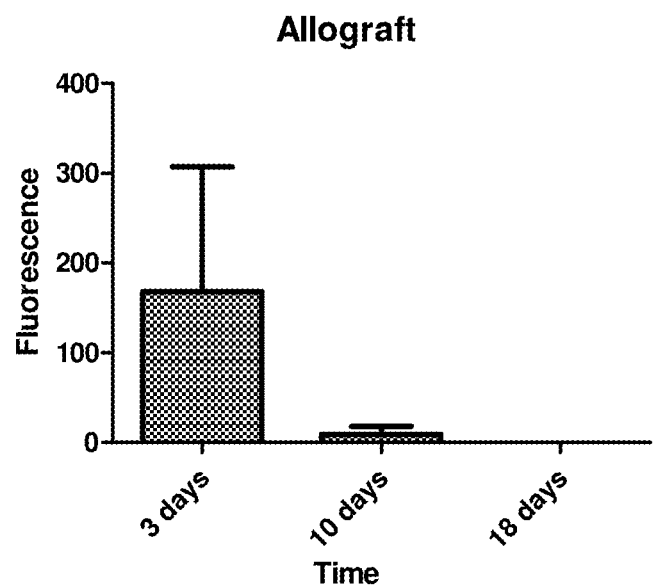
FIG. 1 shows the measured fluorescence, caused by the adhered cells on the surface of the untreated allografts 3, 10 and 18 days following the addition of MSCs.

The term "mineralized bone" in the context of the present invention means that the bone is in its native form in a sense that it contains all of its mineral components and optionally it can contain its organic components as well. In other words the term "mineralized bone" is used to distinguish from demineralized bones in a sense that the mineralized bone is a non-demineralized bone.

In accordance with the meaning as used herein, a bone composition is said to be "substantially cleaned from organic components" e.g. if it was prepared by the method described in the Examples under the "Preparation of freeze-dried mineralized allograft" section or by any other bone mineralization method comprising a washing step performed in an organic solvent and subsequent digestion in an acidic compound. A person skilled in the art would understand that there are numerous ways to produce an equivalent mineralized bone composition.

Coating of allografts with different proteins was surprisingly found to enhance the number of attached MSCs on the surface of the graft, and also supplied the proliferation of cells. The allografts used as scaffolds were cleaned from almost all of the allogenic proteins of the bone in order to decrease the chance of any immunological complications in the host. The removed proteins, like low molecular weight proteins (LMWPs) or bone morphogenetic protein (BMP) are important for the adherence and proliferation of the bone and osteoprogenitor cells (1, 2, 22, 24). Since these proteins had been removed, MSCs could not attach onto the surface of the allograft itself, which mainly consisted of inorganic compounds, like hydroxide-apatite. Present inventors have found that if the removed proteins are replaced with other proteins e.g. with fibronectin, albumin or collagen, preferably and most surprisingly with albumin, then these proteins facilitated the adherence of cells to the surface. Furthermore this facilitated adherence was also observed by using a serum solution. This data shows that surprisingly not just the LMWPs or BMPs can support exclusively the attachment of bone progenitor cells, but other type of proteins as well. Proliferation was observed on the coated to grafts, except on those, which were coated with fibronectin or collagen type I alone. However, the combination of fibronectin with albumin and the combination of collagen type I with fibronectin provides good conditions for the proliferation of MSCs. The best proliferation was observed when FCS was used as a coating material. Proliferation was observed all along the investigation period on those grafts, which were coated with albumin alone or in combination with fibronectin and on those that contained fetal calf serum (FCS).

Our results show that albumin, fibronectin and the serum itself might be the most appropriate coating material for the bone allograft. These coating materials are easily available and supply the adherence and the proliferation of MSCs. It has not escaped our attention that in a preferred embodiment of the invention the albumin, fibronectin, serum and of course the MSCs could be autologous. A scaffold, which is free from the allogenic bone proteins and which contains autologous proteins of serum origin and autologous bone marrow derived MSCs, could incorporate to the host faster than the conventionally used allo-, or autografts and enables an earlier recovery of the patient (9, 10, 11, 17).

Although some MSCs could adhere even on the surface of uncoated allografts, the mineralized bone surface that was cleaned from substantially all BMPs could not provide good conditions for the survival of MSCs (FIG. 1).

Viability of attached cells was investigated with Alamar Blue dye after 3, 10 and 18 days. The color change of Alamar Blue indicated that the attached cells were alive on all of the grafts in the beginning of the experiment. Alamar Blue also indicated that attached cells were not alive, when their number had started to decrease on the grafts. The attached cells' viability was also investigated with Calcein AM fluorescent dye to confirm the results, which were obtained from the measurements with Alamar Blue.

Figure 2A:
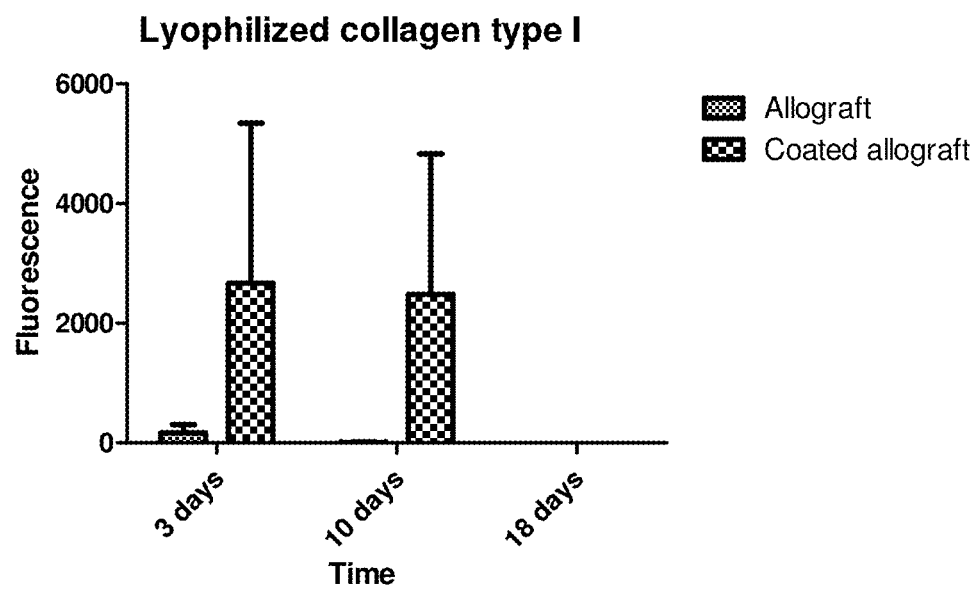
Figure 2B:
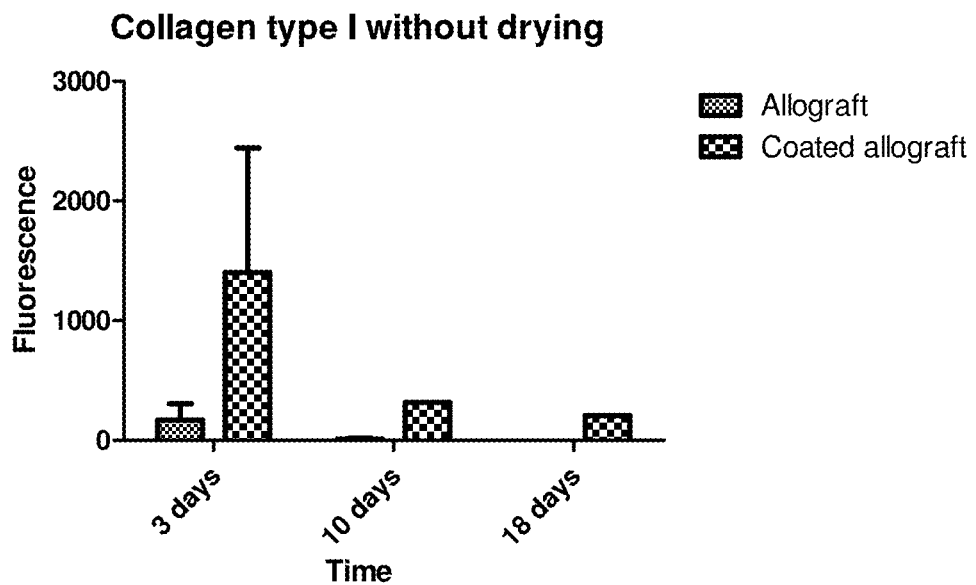
FIG. 2B shows the measured fluorescence 3, 10 and 18 days following the addition of MSCs, caused by the adhered cells on the surface of allografts that were submersed into a collagen type I solution.
Figure 3A:
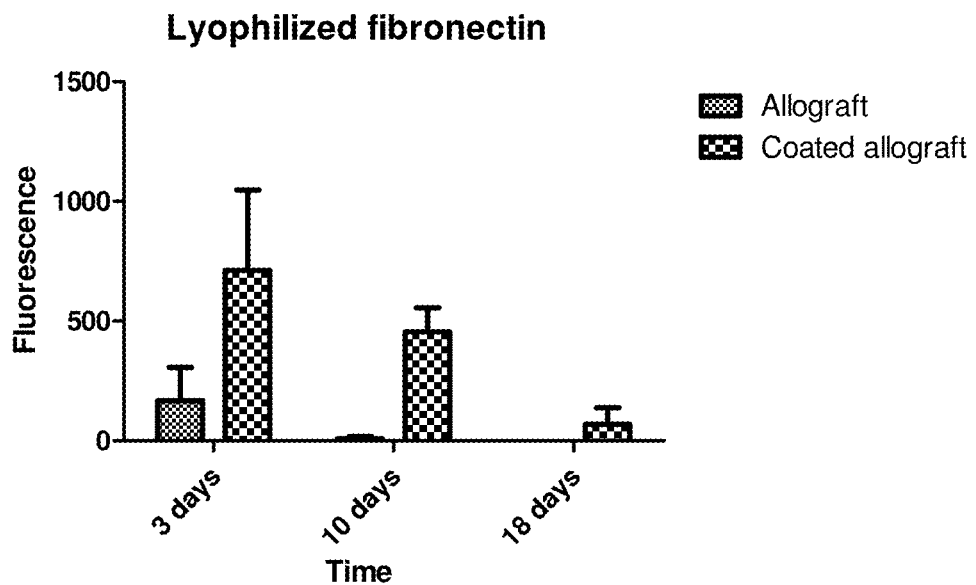
Figure 3B:
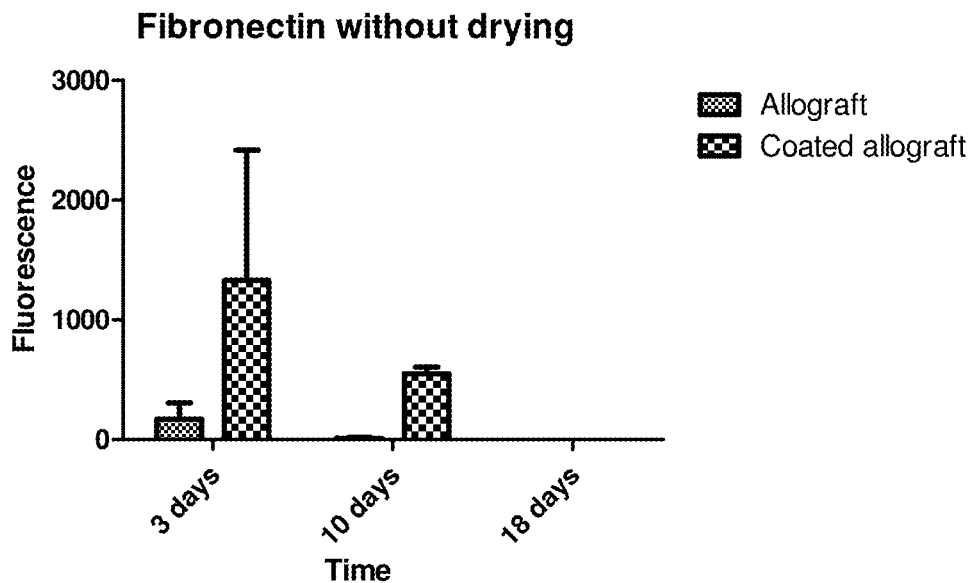
FIG. 3B shows the measured fluorescence 3, 10 and 18 days following the addition of MSCs, caused by the adhered cells on the surface of allografts that were submersed into a fibronectin solution.
Figure 4A:
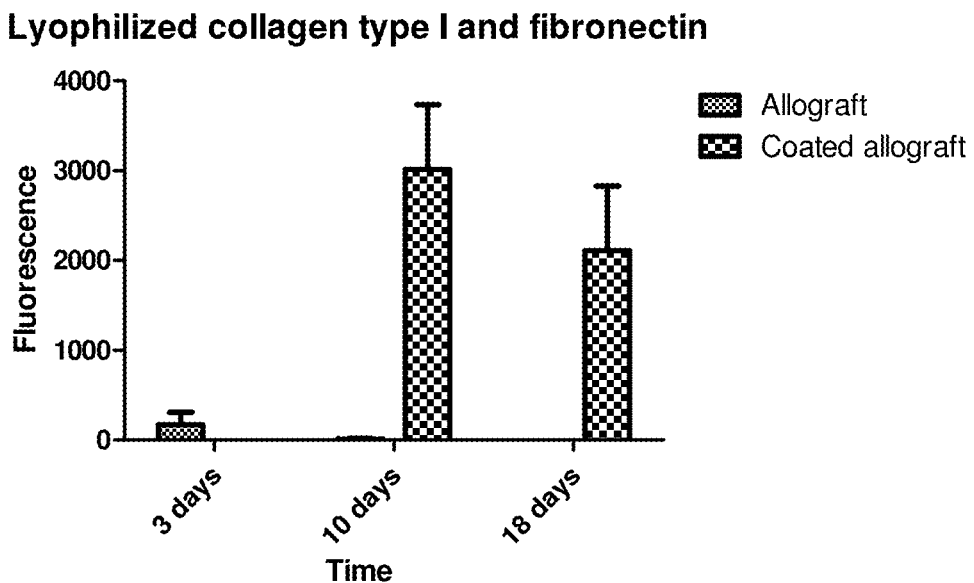
Figure 4B:
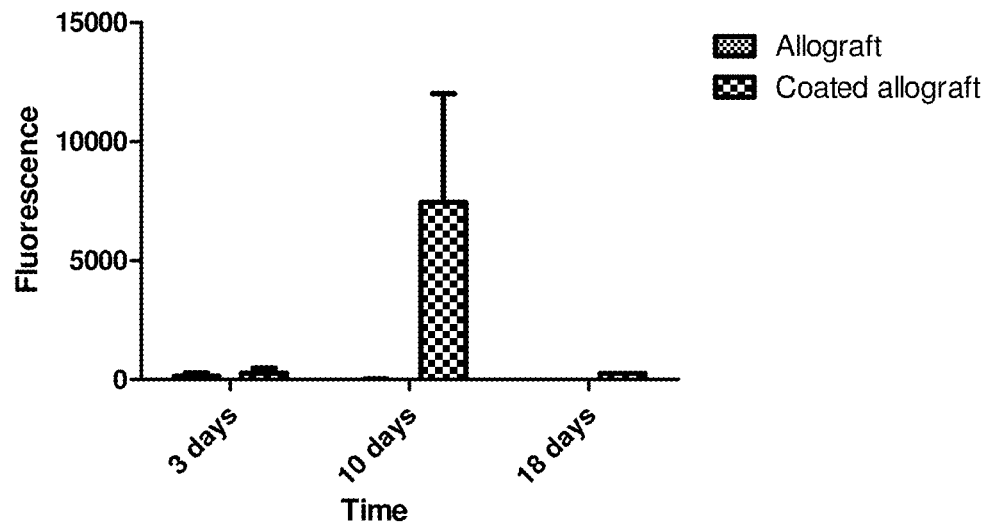
FIG. 4B shows the measured fluorescence 3, 10 and 18 days following the addition of MSCs, caused by the adhered cells on the surface of allografts that were submersed into a collagen type I and fibronectin solution.
Figure 5:
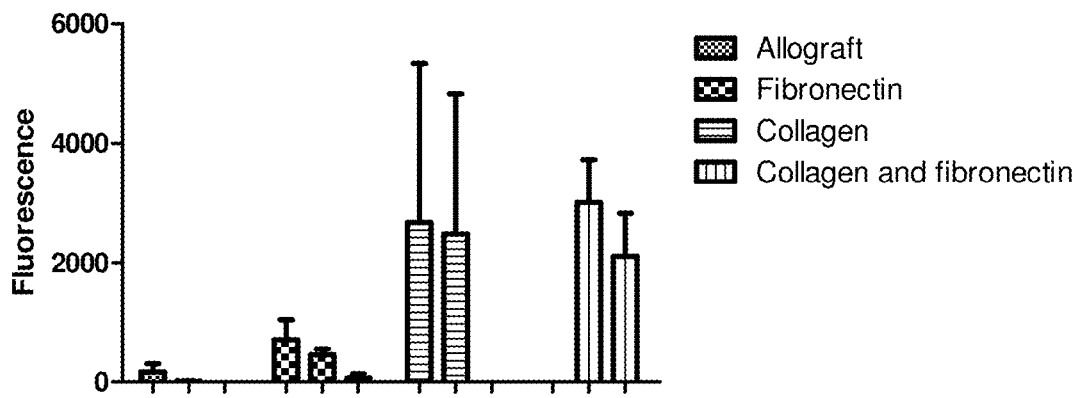
FIG. 5 shows the comparison of the measured fluorescence, caused by the albumin free coating materials.

Collagen type I could not supply the survival of MSCs however it facilitated their adherence on the grafts (FIGS. 2A, B). Although fibronectin is commonly used to support the attachment of cells to different surfaces it facilitated neither adherence nor expansion of the MSCs on mineralized bone allografts (FIGS. 3A, B). On those grafts that contained fibronectin and collagen type I in combination, proliferation was observed in the beginning but the cells did not show metabolic activity after 10 days (FIGS. 4A, B). The moisture content of the used protein compositions did not influence the results. These data show that although fibronectin and collagen type I are important bone structure proteins they themselves could not generate appropriate milieu for the survival of MSCs (FIG. 5).

Figure 6A:
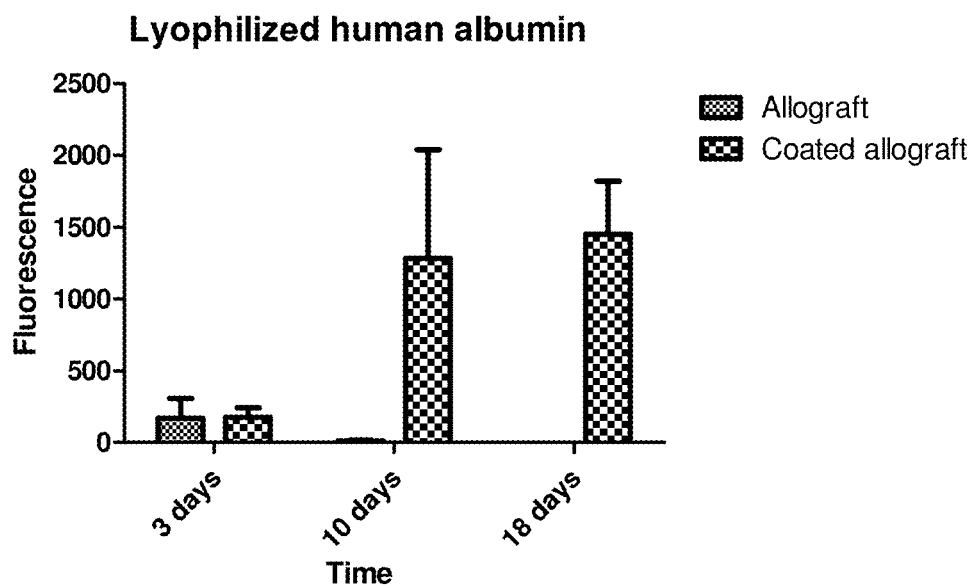
Figure 6B:
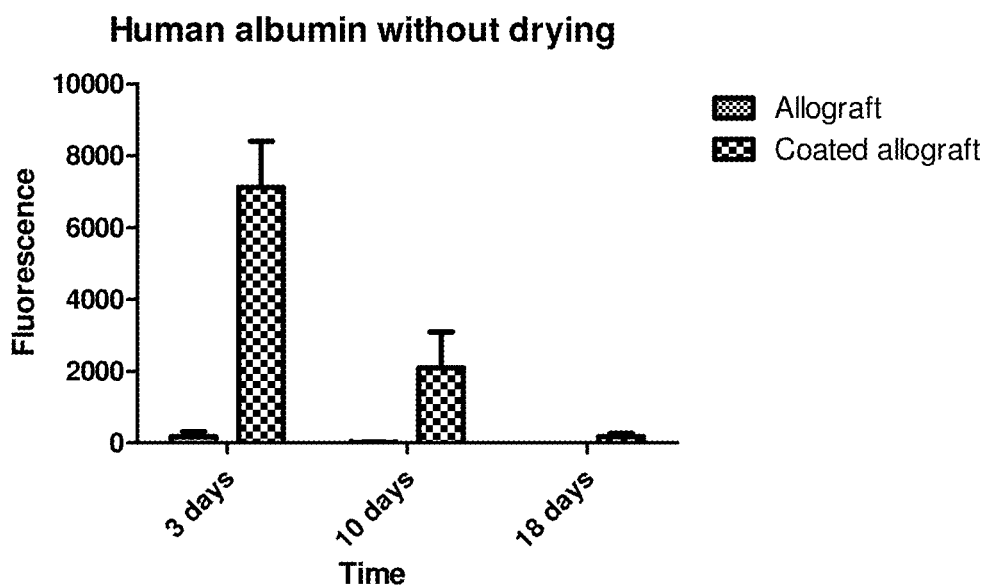
FIG. 6B shows the measured fluorescence 3, 10 and 18 days following the addition of MSCs, caused by the adhered cells on the surface of allografts that were submersed into a human albumin solution.
Figure 7A:
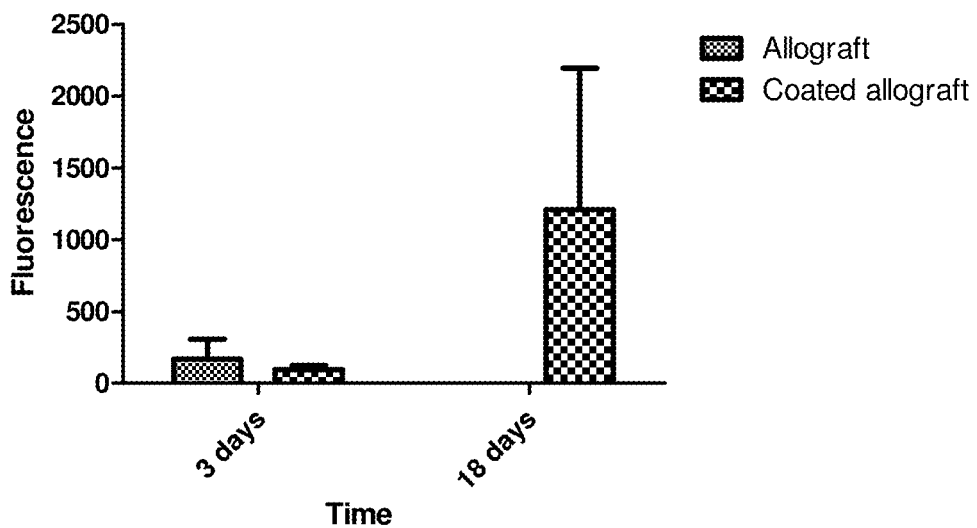
Figure 7B:
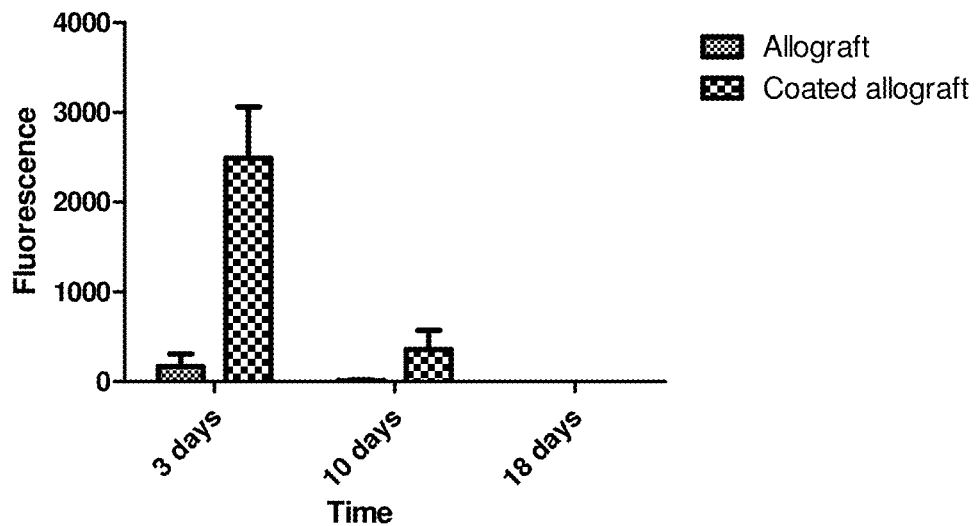
FIG. 7B shows the measured fluorescence 3, 10 and 18 days following the addition of MSCs, caused by the adhered cells on the surface of allografts that were submersed into a human albumin and fibronectin solution.
Figure 8A:
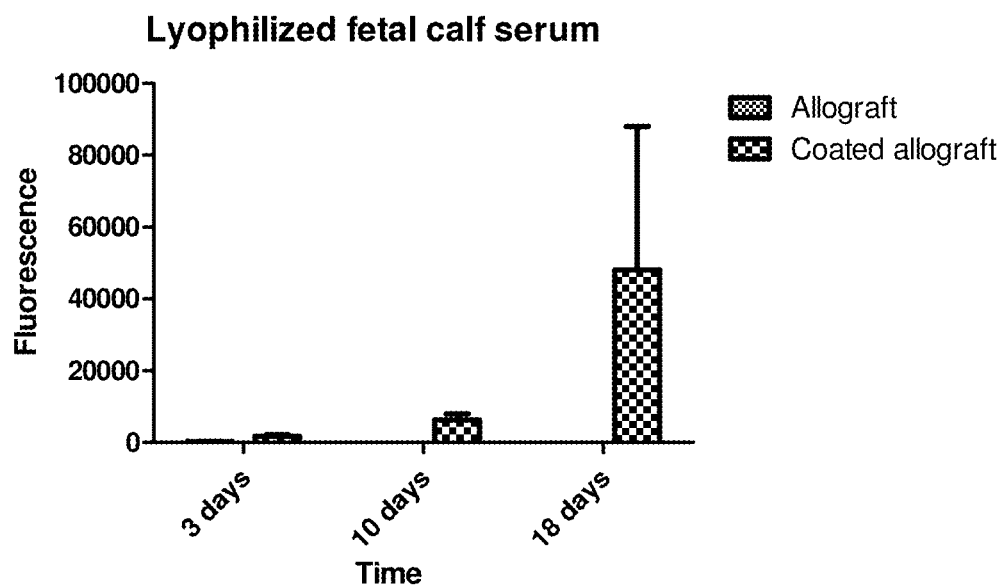
Figure 8B:
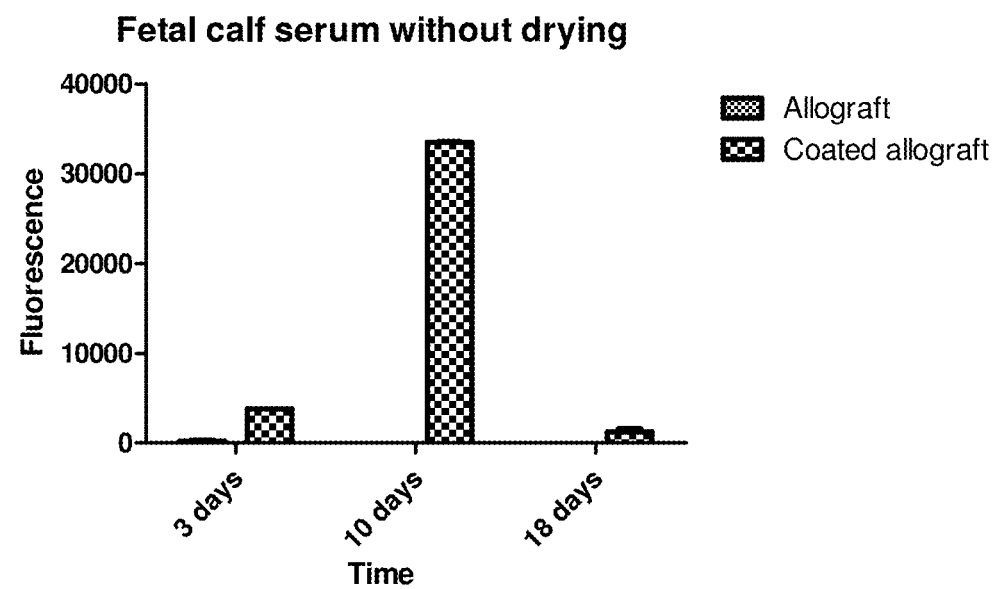
FIG. 8B shows the measured fluorescence 3, 10 and 18 days following the addition of MSCs, caused by the adhered cells on the surface of allografts that were submersed into a fetal calf serum solution.

Surprisingly the presence of lyophilized albumin alone or in combination with other dried proteins of serum origin on grafts enhanced the number of attached MSCs and they provided good conditions for the proliferation of cells all along the experimental period. When albumin or albumin-laden coating proteins were not subjected to freeze-drying on grafts after incubation in protein solution, the amount of cells decreased all along during the experimental period (FIGS. 6B, 7B, 8B).

Figure 9:
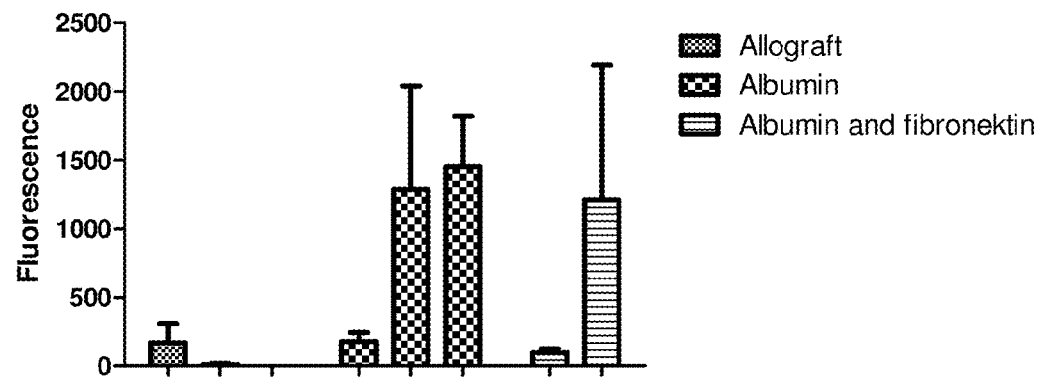
FIG. 9 shows the comparison of the measured fluorescence, caused by the albumin containing coating materials.

Onto those grafts that were coated with lyophilized albumin alone did not attach much more MSCs than on untreated allografts. However we observed that there was a significant difference and this was that albumin facilitated the proliferation of MSCs (FIG. 6A). Combination of lyophilized albumin and fibronectin supplied the adherence and expansion of MSCs as well (FIG. 7A). The highest proliferation rate in the last 8 days of the experiment was seen on those grafts that contained lyophilized fetal calf serum (FIG. 8A) (data not showed on FIG. 9).

In conclusion our data show that coating of mineralized bone particles with serum and/or albumin not only supports stem cell attachment onto mineralized bone allografts, but also supports cell proliferation. Therefore a reliable coating method was developed by the present inventors which coating method makes the surface of bone allografts, preferably mineralized and/or lyophilized bone allografts, appropriate to supply the attachment and survival of MSCs.

EXAMPLES

Source of used materials

| | |
|---|---|
| Dulbecco's Modified Eagle's Medium | Biochrom AG, Germany |
| Fetal calf serum | Gibco, Invitrogen, USA |
| Penicillin-streptomycin | Biochrom AG, Germany |
| L-glutamine | Biochrom AG, Germany |
| Human albumin | BIOTEST HUNGÁRIA KFT., Hungary |

-continued

| | |
|---|---|
| 1000 ml solution contains: Human plasma protein 200 g of which albumin is at least 96% | |
| Fibronectin | Sigma Aldrich |
| Collagen type I | pig collagen, 1.5%, Biom' up, France |
| Vybrant dyes | Molecular Probes, Invitrogen, USA |
| Calcein AM | Molecular Probes, Invitrogen, USA |
| Alamar Blue | Biosource, Invitrogen, USA |

The percentages in the present description if otherwise not stated are always weight/weight percentages.

Example 1

Preparation and Investigation of Allografts

Isolation and Culture of Mesenchymal Stem Cells

Bone marrow derived mesenchymal stem cells (MSCs) were isolated from human bone marrow, and were expanded in DMEM culture medium containing 10% fetal calf serum, 2 mM L-glutamine, 100 U/ml penicillin and 100 µg/ml streptomycin. The bone marrow samples were obtained from young males and females aged 2-20. Only such tissues were used, that otherwise would have been discarded. Semmelweis Orthopedic Clinic Management Committee, Budapest, Hungary, approved the use of these tissues. The bone marrow was taken into T75 flasks, and diluted with DMEM culture medium. This mixture was stored in incubator at 37° C. in 5% $CO_2$ for 3 days. After the incubation time, the MSCs adhered to the surface of the flask and the remnant components of bone marrow were eliminated by washing with PBS. The used cells were between 1 and 5 passages during the experiment.

Characterization of MSCs

The identity of the adhered cells was confirmed by the presence of lineage-specific cell surface markers with flow citometry (BD® FacsCalibur, Beckton Dickinson, N.J., USA). Haemapoetic linage-specific surface markers, like CD34, CD45 and mesenchymal surface markers, like CD73, CD90, CD105 and CD166 were investigated.

Preparation of Freeze-Dried Mineralized Allograft

The used bones were obtained from cadavers or from surgical intervention. In the first step, the bones were washed in methanol for 4 hours. The methanol was changed continually during the procedure. After washing, the bones were digested in a solution that consisted of 0.1 M phosphate buffer saline (PBS), 10 mM sodium-azide and 10 mM monoiodineacetic acid for 24 hours. Subsequently, the bones were subjected to partial decalcification with 0.6 M HCl at room temperature for 4 to 6 hours and then they were washed in PBS. The produced mineralized bone structures (matrices) were sterilized in ethylene-dioxide at 27° C. and then they were freeze-dried (lyophilized) aseptically. Process of the lyophilization: primer drying at 32° C., 2 Pa for 12 hours; second drying at 32° C., 0 Pa for 12 hours.

Preparation of Coated Allograft

The mineralized allograft was frittered into cubic or round shape pieces. The superficies of the allograft pieces was one square centimeter and their height was 5 millimeters. Thus prepared allografts were incubated in protein solution at +4° C. overnight. The used protein solutions were 10-20 µg/ml fibronectin and 10-20% albumin of human serum origin, furthermore fetal calf serum and 1.5% collagen type I was derived from pig. The proteins were also used in combination, like fibronectin with albumin, fibronectin with collagen type I. These bones were used either directly for the "without drying" experiments, or subsequently, the incubated bones were lyophilized at 32° C., at 1 Pa for 24 hours. The coated allografts were subjected to UV irradiation for decontamination for 30 minutes.

Preparation of the Coated Allograft with Stem Cells

The seeded MSCs were labeled with the fluorescent membrane dye Vybrant DID (excitation/emission: 644/665 nm) for 30 minutes at 37° C. DID-labeled MSCs were suspended in DMEM culture medium, and dropped with pipette to the surface of the coated allografts. 60.000 cells/scaffold were used in all the experiments. The MSCs were expanded on the allograft in vitro for 18 days.

Investigation of the Seeded MSCs

The seeded DiD-labeled MSC's proliferation was observed with confocal microscopy (Zeiss LSM 510 META, Carl Zeiss, Jena, Germany) on the coated allograft. Individual areas of the graft were randomly selected, where the amount of the adhered cells were measured by fluorescence. The viability of the cells was investigated with Alamar Blue and Calcein AM dye.

Example 2

Animal Bone Coated with Freeze-Dried Human Albumin

Preparation and Coating of Rat Bone Allografts

Wistar rat (400-450 g) femurs were harvested to use them as rat bone allografts. Following the removal of bone marrow the rat femurs were milled to homogenous bone particles with a diameter of 1 mm Subsequently, the obtained rat bone particles were immersed into human albumin solution and incubated at +4° C. overnight then the human albumin was freeze-dried onto the surface of said bone particles. The conditions of the freeze-drying: 32° C., at 0.5 Pa for 24 hours.

Retrieval of Rat Bone Marrow Derived Stem Cells

Wistar rat (400-450 g) femurs were harvested to retrieve bone marrow derived stem cells. After the harvest of rat femurs their proximal and distal ends were dissected and the bone marrow was flushed into Petri-dishes using DMEM culture medium comprising 10% FCS, 100 U/ml penicillin and 10 µg/ml streptomycin, 2 mM L-glutamine and 1 g/l glucose. The adhered cells at the bottom of Petri-dishes were cultured at 37° C. in fully humidified atmosphere of 5% $CO_2$ (standard culture conditions) until the cells became confluent. Subsequently, the cells were trypsinized and 80.000 cells were seeded on the surface of single rat bone allografts coated with freeze-dried human albumin Bone grafts prepared in this manner were stored under standard cell culture conditions for 7 days then the viability of attached cells was investigated with Calcein AM fluorescent dye using confocal microscope (Zeiss LSM 510 META, Carl Zeiss, Jena, Germany).

Results

Figure 10A:
Figure 10B:
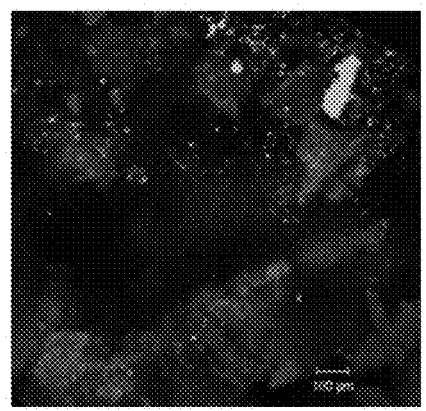
FIG. 10B shows the adhered, viable rat bone marrow derived stem cells on the surface of rat bone allograft coated with lyophilized human albumin.

We found that the rat bone allografts coated with freeze-dried human albumin provided adequate conditions for the attachment and survival of stem cells on the surface during the incubation period (FIGS. 10A, B).

Example 3

Animal Model

Materials and Methods

The osseointegration ability of lyophilized bone grafts coated with freeze-dried human serum albumin was investigated in an animal model. In the first stage of the study a psuedoarthrosis model was developed. On Wistar rats' (400-450 g) femur a 2-3 mm wide transverse middiaphyseal osteotomy had been performed then the bone ends were fixed by plate and screws. Polymethyl methacrylate (PMMA) spacer was placed between the osteotomy sites and the periosteum was removed from the prepared femur to block natural bone healing. After 4 weeks the operation the PMMA plate was removed and the osteotomy gap was left empty further 4 weeks. Following 4 weeks post-operative period the animals were sacrificed and their femurs were harvested and subjected to µCT examination to prove the development of a pseudarthrosis. In the second stage, the pseudoarthrosis model was prepared just as above detailed, but following the removal of the PMMA spacers uncoated lyophilized bone allografts (as control) and coated with freeze-dried human albumin were implanted into the osteotomy gaps. 4 weeks after the implantation of bone grafts the animals were sacrificed and the harvested femurs were subjected to µCT examination (25).

Results

Figure 11A:
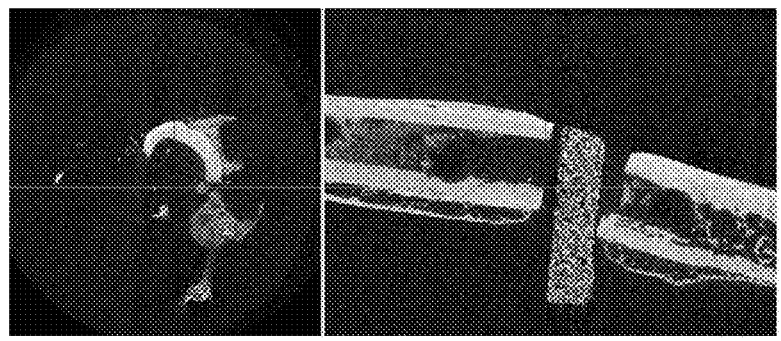
Figure 11B:
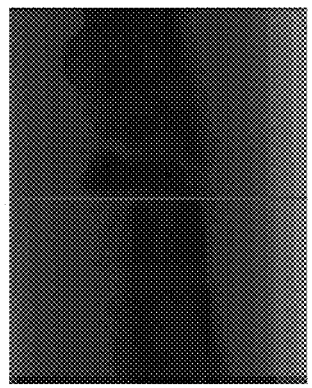

New bone formation was not observed in the osteotomy gaps which were left empty following the removal of PMMA spacer. This proves that the model is suitable for the investigation of the osseointegration ability of the bone grafts according to the present invention (FIGS. 11A, B).

Figure 11C:
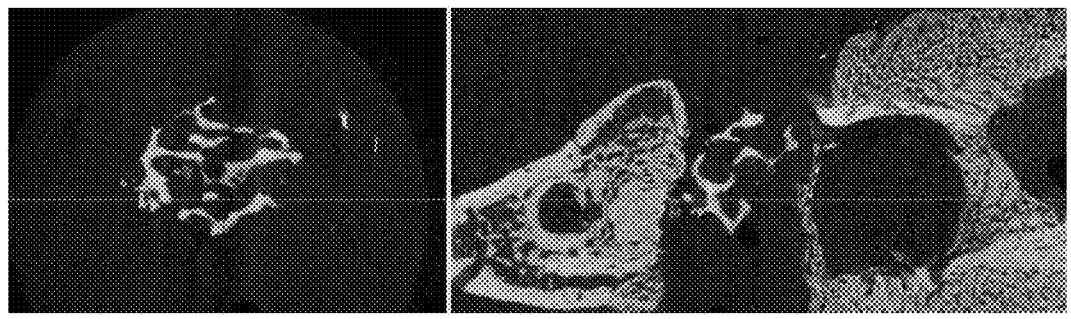
FIG. 11C-D show that the non-coated lyophilized human bone allograft did not facilitate new bone tissue formation therefore it could not integrate into the site to of bone defect.
Figure 11D:
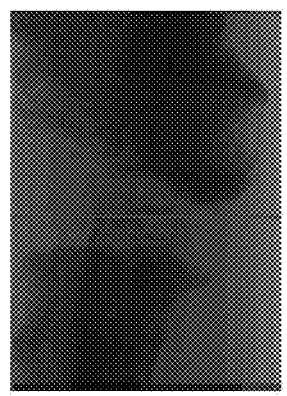
Figure 12A:
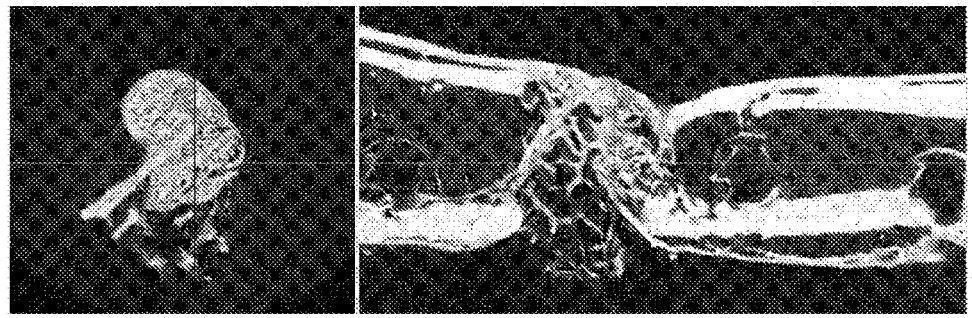
FIG. 12A-B shows that a human bone graft coated with freeze-dried human albumin advanced new bone formation in the osteotomy gap following 4 weeks the implantation.
Figure 12B:
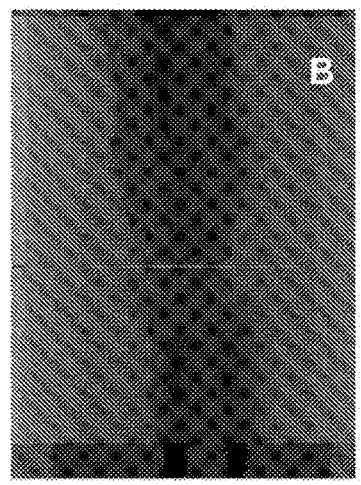

The uncoated lyophilized bone allografts (controls) were not able to integrate into the site of bone defects (FIGS. 11C, D). On the other hand, bony fusion can be detected 4 weeks after the implantation of the albumin lyophilized human bone graft. The cancellous bone between the osteotomy edges with a loose structure and wider holes refers to the remnants of the implanted graft. The x-ray shows heeling of the defect (FIGS. 12A, B).

Example 4

Serum Albumin Markedly Increases Bone Formation In Vivo

Blood serum fractions such as platelet rich plasma or activated serum are possible adjuvants in bone replacement therapies. In the previous examples we have shown that serum albumin coating on bone allografts can significantly increase stem cell adherence and proliferation in vitro, raising the possibility that serum albumin alone may be an effective autologous agent in bone remodeling. We also investigated the bone formation by filling critical size defects with serum albumin coated allografts in a rat cranial defect model.

Materials and Methods

Under ketamine/xylazine anesthesia 3.5 mm bone defects were created on the cranium of Wistar rats with a trephine bur. Mineralized bone allografts coated with serum albumin were used to fill the defect. Uncoated bone grafts served as positive controls and defects left empty served as negative controls. After 1, 3, 5, 7, 9, 11 weeks postoperatively computed tomography (CT) was performed in order to follow bone formation. Bone density and the area of the remaining defect were calculated. At the $11^{th}$ week parietal bones were harvested and engraftment was tested with an Instron 5566 mechanical testing machine. All methods, including surgery and evaluations were performed according to Nature Protocols [26].

Figure 13:
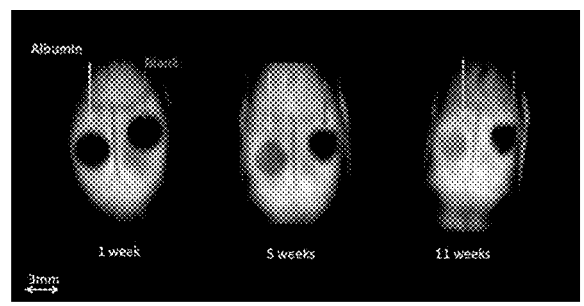
FIG. 13 shows horizontal reconstructional CT images of bone formation after 1, 5 and 11 weeks (Example 4). Yellow arrows indicates ossification of albumin coated grafts, red arrows show defects left empty (sham).

Results:

CT scan showed bone formation already after three weeks in every experimental group (FIG. 13). At five weeks significant difference can be observed between the control groups and the albumin-coated group. The remaining bone defect in the albumin-coated group was 15.21%±6.57, while in the control groups it was significantly larger (uncoated: 63.4%±12.8 to and sham 62.07%±7.8). Furthermore, in the albumin-coated group every bone defect healed completely by the 9th week while a significant defect was still present in the control groups (uncoated: 29.6%±8.4; sham: 43.6%±8.8). Bone formation was also measured by densitometry: from the 5th week the albumin-coated group showed markedly higher values compared to the controls. By the 11th week the defects treated with the albumin coated graft reached over 1000 Hounsfield unit (1061.25 HU±79.1), while density in the control groups were 699.9±104.6 HU (uncoated) and 655.70 HU±84.04 HU (sham). In addition, albumin coated grafts showed significantly higher breaking force values after mechanical testing compared to the uncoated grafts (albumin 46.1±10 N, uncoated 15.7N±5 N).

Conclusions:

In the present example we showed that implanting serum albumin coated allografts significantly reduce healing time in critical size defects. These results also support the idea that albumin coating provides a convenient milieu for stem cell function, therefore cell therapy can be achieved without the use of exogenous stem cells.

LIST OF REFERENCES

1. MARK E. BOLANDER, GARY BALIAN: Use of demineralized bone matrix in the repair of segmental defects. U.S. Pat. No. 4,743,259, 10 May 1988.
2. MARK E. BOLANDER, GARY BALIAN: Use of demineralized bone matrix in the repair of segmental defects. U.S. Pat. No. 4,902,296, 20 Feb. 1990.
3. BARBARA L. MERBOTH, MOON HAE SUNWOO, ARTHUR A. GERTZMAN: Allograft bone composition having gelatin binder. U.S. Pat. No. 704,514, 16 May 2006.
4. RUST P A, KALSI P, BRIGGS T W, CANNON S R, BLUNN G W: Will mesenchymal stem cells differentiate into osteoblasts on allograft? Clin Orthop Relat Res. 2007 April; 457:220-6.
5. BENJAMIN J R F BOLLAND, KRIS PARTRIDGE, SIMON TILLEY, ANDREW M R NEW, DOUGLAS G DUNLOP AND RICHARD O C OREFFO: Biological and mechanical enhancement of impacted allograft seeded with human bone marrow stromal cells: potential clinical role in impaction bone grafting. Regenerative Medicin. July 2006, Vol. 1, No. 4, Pages 457-467.
6. KAI-UWE LEWANDROWSKI, SHRIKAR BONDRE, DEBRA J. TRANTOLO, MAURICE V. CATTANEO, JOSEPH D. GRESSER, DONALD L. WISE: Osteoinduction of cortical bone allografts by coating with biopolymers seeded with recipient periosteal bone cells. U.S. Pat. No. 6,899,107 B2, 31 May 2005.
7. VALERIE OLIVIER, NATHALIE FAUCHEUX and PIERRE HARDOUIN: Biomaterial challenges and approaches to stem cell use in bone reconstructive surgery. Drug Discov Today. 2004 Sep. 15; 9(18):803-11. Vol. 9, No. 18 September, 2004.
8. RICHARD O. C. OREFFO, FERDINAND C. M. DRIESSENS, JOSEPH A. PLANELL and JAMES T. TRIFFITT: Growth and differentiation of human bone marrow osteoprogenitors on novel calcium phosphate cements. Biomaterials. 1998 October; 19(20):1845-54.
9. PERRY C R: Bone repair techniques, bone graft, and bone graft substitutes. Clin Orthop Relat Res. 1999 March; (360):71-86. Review.
10. GIANNOUDIS PV, DINOPOULOS H, TSIRIDIS E.: Bone substitutes: an update. Injury. 2005 November; 36 Suppl 3:S20-7. Review.
11. KARIN A. HING: Bone repair in the twenty-first century: biology, chemistry or engineering? Philos Transact A Math Phys Eng Sci. 2004 Dec. 15; 362(1825):2821-50. Review 12. LEWANDROWSKI K U, GRESSER J D, WISE D L, TRANTOL D J: Bioresorbable bone graft substitutes of different osteoconductivities: a histologic evaluation of osteointegration of poly(propylene glycol-co-fumaric acid)-based cement implants in rats. Biomaterials. 2000 April; 21(8):757-64.
13. WAHL D A, CZERNUSZKA J T: Collagen-hydroxyapatite composites for hard tissue repair. Eur Cell Mater. 2006 Mar. 28; 11:43-56. Review
14. ARRINGSTON E D, SMITH W J, CHAMBERS H G, BUCKNELL A L, DAVINO N A: Complications of iliac crest bone graft harvesting. Clin Orthop Relat Res. 1996 August; (329):300-9.
15. KÖRBLING M, CHAMPLIN R: Peripheral blood progenitor cell transplantation: a replacement for marrow auto- or allografts. Stem Cells. 1996 March; 14(2):185-95. Review.
16. CHERN B, McCARTHY N, HUTCHINS C, DURRANT S T: Analgesic infiltration at the site of bone marrow harvest significantly reduces donor morbidity. Bone Marrow Transplant. 1999 May; 23(9):947-9.
17. PARIKH S N: Bone graft substitutes: past, present, future. J Postgrad Med. 2002 April-June; 48(2):142-8.
18. DODD C A, FERGUSSON C M, FREEDMAN L, HOUGHTON G R, THOMAS D: Allograft versus autograft bone in scoliosis surgery. J Bone Joint Surg Br. 1988 May; 70(3):431-4.
19. SUMMERS B N, EISENSTEIN S M: Donor site pain from the ilium. A complication of lumbar spine fusion. J Bone Joint Surg Br. 1989 August; 71(4):677-80.
20. SAMPATH T K, REDDI A H: Dissociative extraction and reconstitution of extracellular matrix components involved in local bone differentiation. Proc Natl Acad Sci USA. 1981 December; 78(12):7599-603.
21. REDDI A H: Interplay between bone morphogenetic proteins and cognate binding proteins in bone and cartilage development: noggin, chordin and DAN. Arthritis Res. 2001; 3(1):1-5. Epub 2000 Nov. 14. Review.
22. TULI, S, M., and SINGH, A. D.: The Osteoinductive Property of Decalcified Bone Matrix. An experimental study. J. Bone and Joint Surg., 60-B: 116-123, 1978.
23. URIST, M. R., IWATA, H., CRECCOTT, P. L., DORFMAN, R. L., BOZD, S. D., MCDOWELL, R. M., and CHIEN, C.: Bone Morphogenesis in implants of Insoluble Bone Gelatin. Proc. Natl. Acad. Sci. U.S.A., 70: 511, 1973.
24. TAKAGI K, URIST M. R.: The reaction of the dura to bone morphogenetic protein (BMP) in repair of skull defects. Ann Surg. 1982 July; 196(1):100-9.
25. SCHMIDHAMMER R, ZANDIEH S, MITTERMAYR R, PELINKA L E, LEIXNERING M, HOPF R, KROEPFL A, REDL H. Assessment of bone union/nonunion in an experimental model using microcomputed technology. J Trauma. 2006 July; 61(1):199-205.
26. PATRICK P SPICER, JAMES D KRETLOW, SIMON YOUNG, JOHN A JANSEN, F KURTIS KASPER, ANTONIOS G MIKOS (2012) Nature Protocols Nature America, Inc. October; 7(10):1918-29.

The invention claimed is:

1. An implantable bone graft composition comprising bone particles coated with dried albumin said bone graft composition produced by incubating bone particles with a protein solution comprising albumin wherein the concentration of albumin in said solution is in the range of 1% to 50% by weight and drying said solution onto said bone particles, wherein in the presence of coated dried albumin on their surface, said bone particles exhibit enhanced stem cell attachment and stem cell proliferation of stem cells seeded onto their surfaces as related to bone particles coated with albumin without drying.

2. The implantable bone graft composition of claim 1, wherein said graft composition is produced by incubating bone particles with a protein solution comprising albumin wherein the concentration of albumin in said solution is in the range of 1% to 50% by weight and freeze-drying said solution onto said bone particles, wherein in the presence of coated freeze-dried albumin on their surface, said bone particles exhibit enhanced mesenchymal stem cell attachment and stem cell proliferation of mesenchymal stem cells seeded onto their surfaces as related to freeze-dried coated bone particles with fibronectin or collagen.

3. The implantable bone graft composition of claim 1, wherein albumin is present at about 10% by weight of the composition so as to result in loose bone chips or bone blocks not in the form of a conglomerate malleable mass.

4. The implantable bone graft composition according to claim 1 wherein said albumin is human albumin.

5. The implantable bone graft composition according to claim 4 wherein said human albumin is of serum origin.

6. The implantable bone graft composition according to claim 1 wherein said protein solution comprises at least one ingredient which is of human origin or is immunologically humanized.

7. The implantable bone graft composition according to claim 1 wherein said protein solution is obtained from a patient in need of a bone implantation.

8. The implantable bone graft composition according to claim 7 wherein said protein solution comprises serum of said patient or any fraction thereof.

9. The implantable bone graft composition according to claim 1 wherein said protein solution comprises a recombinant protein.

10. The implantable bone graft composition according to claim 1 wherein said protein solution further comprises fibronectin or collagen or combination thereof.

11. The implantable bone graft composition according to claim 1 wherein said protein solution is free from components being potentially immunogenic to the patient intended to receive said mineralized bone composition as an implant.

12. The implantable bone graft composition according to claim 1 wherein said bone particles are lyophilized bone particles.

13. The implantable bone graft composition according to claim 1 wherein said bone particles are mineralized bone particles being substantially cleaned from organic components, and wherein the implantable bone graft composition does not contain demineralized bone.

14. The implantable bone graft composition according to claim 1, wherein the stem cells are mesenchymal stem cells.

15. The implantable bone graft composition according to claim 14 wherein said mesenchymal stem cells are obtained from the patient intended to receive said bone transplantation.

16. A method for enhancing osteointegration ability of bone grafts and, thereby, speed of bone healing after bone grafting, said method comprising the following steps:
    a) producing an implantable bone graft composition according to claim 1,
    b) implanting the bone graft produced in step a) into a patient in need of a bone implantation.

17. The implantable bone graft composition of claim 1, wherein the concentration of albumin in said solution is in the range of 3% to 30% by weight.

* * * * *